United States Patent [19]

Frenier et al.

[11] E Re. 30,283

[45] Reissued * May 27, 1980

[54] SULFONIUM COMPOUNDS AS CORROSION INHIBITORS IN AQUEOUS ACIDIC CLEANING SOLUTIONS

[75] Inventors: Wayne W. Frenier, Tulsa, Okla.; William J. Settineri, Midland, Mich.

[73] Assignee: The Dow Chemical Company, Midland, Mich.

[ * ] Notice: The portion of the term of this patent subsequent to Oct. 9, 1990, has been disclaimed.

[21] Appl. No.: 11,745

[22] Filed: Feb. 13, 1979

Related U.S. Patent Documents

Reissue of:

[64] Patent No.: 4,101,438
Issued: Jul. 18, 1978
Appl. No.: 669,116
Filed: Mar. 22, 1976

U.S. Applications:

[63] Continuation of Ser. No. 350,295, Apr. 11, 1973, abandoned, which is a continuation-in-part of Ser. No. 118,175, Feb. 23, 1971, Pat. No. 3,764,543.

[51] Int. Cl.[2] ..... C11D 7/34; C23G 1/06

[52] U.S. Cl. ..... 252/151; 252/87; 252/145; 252/146; 252/136; 252/147; 252/149; 252/391; 252/394; 252/395; 422/12

[58] Field of Search ..... 252/151, 181, 87, 136, 252/145, 146, 149, 394, 395, 291; 422/12

[56] References Cited

U.S. PATENT DOCUMENTS 3,996,147 12/1976 Settineri et al. ..... 252/149

*Primary Examiner*—Mayer Weinblatt
*Attorney, Agent, or Firm*—L. Wayne White; James B. Guffey

[57] ABSTRACT

Certain sulfonium salts are herein described which are useful corrosion inhibitors in aqueous acidic cleaning solutions, even in the presence of ferric ions. The sulfonium salts correspond to the following formulas:

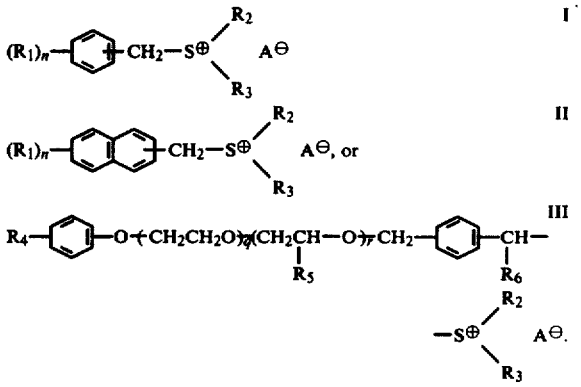

20 Claims, No Drawings

SULFONIUM COMPOUNDS AS CORROSION INHIBITORS IN AQUEOUS ACIDIC CLEANING SOLUTIONS

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation of our U.S. patent application Ser. No. 350,295 filed Apr. 11, 1973 (now abandoned) which is a continuation-in-part of our U.S. patent application Ser. No. 118,175 filed Feb. 23, 1971 (and is now USP 3,764,543).

BACKGROUND OF THE INVENTION

Iron oxide encrustations, commonly known as rust or iron oxide scale, frequently form on ferrous metal surfaces. Such surface deposits are objectionable on ferrous articles which are scheduled to be refinished (e.g. sheet steel) and are particularly troublesome when located on the surfaces of tubing and other conduits (e.g., boiling tubing, heat exchangers, connecting piping, and the like) wherein the deposits can restrict flow and interfere with heat exchange.

Various methods of removing such surface deposits have been devised, a common one being to contact the ferrous surface with an aqueous acidic cleaning solution (e.g. aqueous HCl) and thereby dissolve and remove the iron oxide encrustations from the surface. An iron salt typically results from this operation, the specific salt depending upon the acidic cleaning medium used. E.g., $FeCl_3$ and/or $FeCl_2$ are formed when HCl is used.

Such iron salts are generally soluble to at least a limited extent in the cleaning media. Ferric ions thus result.

Corrosion of ferrous metal surfaces in contact with aqueous acids is known. It is also known that the presence of ferric ion causes severe corrosion problems of ferrous metal surfaces during the above mentioned acid cleaning process. Namely, the cleaning solution attacks (corrodes) the freshly cleaned metal surface with the attendant loss of metal. In the presence of oxygen, ferric ions are continually regenerated accentuating the problem.

Many compounds have been included as corrosion inhibitors in such cleaning solutions but their effectiveness in the presence of ferric ion is generally nonexistent or quite low.

Similarly, the corrosion of other common construction metals (and metal alloys) in contact with aqueous acid solution is a definite problem. E.g., in the above-mentioned process of clearing ferrous metal surfaces with acid solutions, other metals may be present as an integral part of the system being cleaned (e.g. copper, copper alloys, zinc, zinc alloys, stainless steels, etc.), which may be similarly corroded.

It is therefore an object of this invention to inhibit the acid induced corrosion of metal surfaces, particularly ferrous and cuprous metal surfaces, in contact with aqueous acid solutions.

Another object of this invention is to inhibit acid induced corrosion of ferrous metal surfaces even in the presence of ferric ions.

SUMMARY OF THE INVENTION

It has now been discovered that the sulfonium salts represented by I and II below are highly effective in inhibiting the corrosion of metals, particularly ferrous and cuprous metals, in contact with aqueous acid solutions. The sulfonium salts correspond to the formula

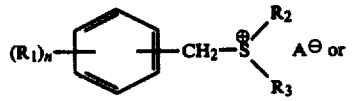

I

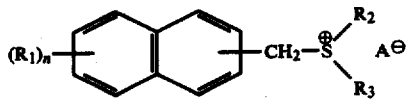

II wherein n is 1 or 2; each $R_1$ independently is hydrogen or a hydrocarbyl, hydrocarbyloxy or hydrocarbylthio radical of from 1 to about 24 carbon atoms; $R_2$ is a hydrocarbyl or inertly-substituted hydrocarbyl radical of from 1 to about 24 carbon atoms, with the proviso that the total aggregate carbon content of $R_1$ and $R_2$ is from 7 to about 25; $R_3$ is an alkyl radical of from 1 to 4 carbon atoms or an inertly-substituted alkyl radical of from 2 to 4 carbon atoms, allyl, phenyl or an inertly-substituted phenyl radical; or $R_2$ and $R_3$ are joined to form a 5- or 6-membered heterocyclic ring, with the proviso that the total aggregate carbon content of $R_1$, $R_2$ and $R_3$ is from 10 to about 25 when $R_2$ is joined with $R_3$ to form a 5- or 6-membered ring; and $A^\ominus$ is an anion.

The sulfonium salts represented by I and II are effective at low concentrations (e.g. 2 to 4 millimoles/liter) and are, surprisingly, effective even in the presence of ferric ions. Thus, the above-described ferric ion corrosion problem experienced during the cleaning of ferrous metal surfaces can be substantially reduced if not eliminated by incorporating into the acidic cleaning solution a small but sufficient amount of said sulfonium salts to produce the desired inhibition effect.

DETAILED DESCRIPTION OF THE INVENTION

The Sulfonium Salts

Suitable sulfonium salts for use herein are represented by I and II above, each of which represents a known class of compounds. Such compounds are typically prepared in a known reaction comprising reacting a "benzyl" halide with an appropriate sulfide, as per the equation:

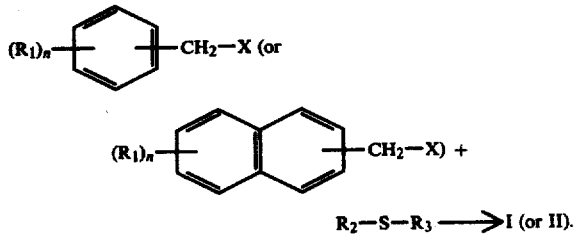

In this illustration, of course, X is halogen (e.g. chloro or bromo) and becomes the anion ($A^\ominus$) in the final product (I or II). The corresponding sulfonium salts containing other anions are then typically prepared by conventional ion-exchange techniques. Other methods of preparing I and II are known to those skilled in the art.

Examples of suitable sulfonium salts are those in I and II wherein:

$R_1$ is hydrogen or a hydrocarbyl radical, such as alkyl (e.g. methyl, ethyl, propyl, butyl, hexyl, octyl, decyl, dodecyl, and the like), aryl (e.g. phenyl, naphthyl, and the like), aralkyl (e.g. benzyl, phenethyl, and the like), alkaryl (e.g. tolyl, 3,5-dimethylphenyl, butylphenyl, and the like), cycloalkyl (e.g. cyclohexyl and the like), alkenyl (e.g. vinyl, allyl, butenyl, hexenyl, and the like); or hydrocarbyloxy, such as alkoxy, aryloxy, alkenyloxy, etc. (e.g. butoxy, phenoxy, p-hydroxyphenoxy, hexylphenoxy, chlorophenoxy, allyloxy, and the like); or hydrocarbylthio radicals, such as alkylthio, arylthio, etc. (e.g. methylthio, ethylthio, butylthio, phenylthio, and the like);

$R_2$ is a hydrocarbyl radical, such as alkyl (e.g. methyl, ethyl, propyl, butyl, hexyl, octyl, decyl, dodecyl, and the like), aryl (e.g. phenyl, hydroxyphenyl and the like), aralkyl (e.g. benzyl, phenethyl phenylbutyl, and the like), alkaryl (e.g. tolyl, 3,5-dimethylphenyl, butylphenyl, hexylphenyl, and the like), cycloalkyl (e.g. cyclohexyl, and the like), alkenyl (e.g. allyl, butenyl, hexenyl, and the like; or $R_3$ is an alkyl radical of from 1 to 4 carbon atoms (i.e. methyl, ethyl, propyl and butyl) or an inertly-substituted alkyl radical of 1 to 4 carbon atoms, allyl, phenyl or inertly-substituted phenyl. By "inertly-substituted" as used in this application is meant that the hydrocarbyl radical bears one or more substituents which are inert to the liquid acidic medium in which the sulfonium corrosion inhibitors are to be used. Such inert substituents include hydroxy, halo, etc. Thus, $R_3$ includes hydroxyalkyl radicals of 1 to 4 carbon atoms, chloroalkyl radicals, and the like;

$R_2$ and $R_3$ can be joined to form, in combination with the sulfonium atom, a 5- or 6-membered heterocyclic ring (such as thiophenium, tetrahydrothiophenium, thiopyrylium and tetrahydrothiopyrylium);

with the proviso that the total aggregate carbon content of $R_1$ and $R_2$ is from 7 to about 25; and, with the additional proviso that the total aggregate carbon content of $R_1$, $R_2$ and $R_3$ is from 10 to about 25 when $R_2$ and $R_3$ are joined to form the 5- or 6-membered heterocyclic rings;

$A^{\ominus}$ is a compatible anion. The choice of anion, $A^{\ominus}$ is not critical and may be varied to convenience. However, the anion is generally chosen to be the same as the acid in solution as a matter of convenience. The anion may be selected by the method of preparing the sulfonium salt or by ion exchange means. Examples of suitable anions include chloride, bromide, iodide, nitrate, bisulfate, tosylate, acetate, benzoate, dihydrogen phosphate, and the like. The ring position of the $R_1$ substituent(s) in I and II is not critical but is preferably at least two ring carbons removed from the $—CH_2—S^{\oplus}R_2R_3A^{\ominus}$ group. E.g. $R_1$ is preferably a meta- or para-substituent (most preferably para) in I.

Preferably, n is 1 in I and II.

$R_1$ is preferably hydrogen, alkyl or alkylphenoxy and is most preferably alkyl of 8 to 18 carbon atoms.

$R_2$ is preferably alkyl, β-hydroxyalkyl of 2 to 4 carbon atoms (i.e. β-hydroxyethyl, β-hydroxypropyl and β-hydroxybutyl), allyl, phenyl or hydroxyphenyl, and is most preferably alkyl, β-hydroxyethyl or allyl.

$R_3$ is preferably alkyl of 1 to 4 carbon atoms, β-hydroxyalkyl of 2 to 4 carbon atoms, allyl, phenyl or hydroxyphenyl, and is most preferably alkyl of 1 to 4 carbon atoms, β-hydroxyethyl or allyl.

The preferred sulfonium salts are, of course, a combination of the above preferences for $R_1$–$R_3$ and n. Likewise, the most preferred sulfonium salts are a combination of the most preferred embodiments for $R_1$–$R_3$ with n being 1. Additionally, the sulfonium salts represented by Formula I are normally preferred over those represented by Formula II.

Representative examples of suitable sulfonium salts for use herein include those in Formula I having the following values for $R_1$–$R_3$ and $A^{\ominus}$.

Table I

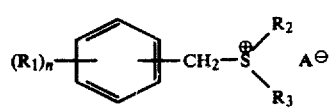

I

| $R_1$ | $R_2$ | $R_3$ | $A^{\ominus}$ |
|---|---|---|---|
| $CH_3$ | $C_{18}H_{37}$ | $CH_3$ | Cl |
| $C_3H_7$ | $C_{10}H_{21}$ | $C_2H_5$ | $HSO_4$ |
| $C_6H_{13}$ | $CH_3$ | $C_6H_5$ | Cl |
| $C_3H_{17}$ | $CH_2{=}CHCH_2$ | $CH_2{=}CHCH_2$ | Br |
| $C_{12}H_{25}$ | $CH_3$ | $CH_2CH_2OH$ | Cl |
| $C_{18}H_{37}$ | $CH_3$ | $CH_3$ | I |
| $C_{20}H_{41}$ | $CH_3$ | $CH_2{=}CHCH_2$ | Cl |
| $C_8H_{17}O$ | $CH_2CH_2OH$ | $CH_2CH_2OH$ | $NO_3$ |
| $C_4H_9S$ | $C_{12}H_{25}$ | $C_3H_7$ | tosylate |
| $C_6H_5$ | $CH_3$ | $CH_3$ | $H_2PO_4$ |
| $C_6H_5O$ | $C_6H_{13}$ | $CH_3$ | acetate |
| $C_4H_9C_6H_4O$ | $CH_2CH_2OH$ | $CH_2CH_2OH$ | Cl |
| $C_8H_{17}C_6H_4O$ | $CH_3CH{=}CHCH_2$ | $C_4H_9$ | Br |
| $C_6H_5CH_2CH_2$ | $C_3H_7$ | $C_3H_7$ | I |
| cyclohexyl | $C_4H_9$ | $CH_3$ | $NO_1$ |
| $C_6H_5S$ | $CH_3$ | $C_6H_5OH$ | Cl |
| H | $C_6H_5CH_2CH_2$ | $CH_3$ | $HSO_4$ |
| $CH_2{=}CH$ | $C_{18}H_{37}$ | $CH_3$ | Cl |
| $CH_2{=}CHCH_2$ | $C_{12}H_{25}$ | $C_2H_4$ | Cl |
| $CH_2{=}CHCH_2—O—$ | $C_6H_{13}$ | $CH_3$ | I |
| 3-ethyl, 5-ethyl | $C_8H_{17}$ | $CH_2CH_2OH$ | Cl |
| 2-methyl, 4-methyl | $C_{18}H_{37}$ | $CH_3$ | Br |

The sulfonium compounds within Formula II having corresponding $R_1$–$R_3$ and $A^{\ominus}$ values are likewise representative compounds of the sulfonium salts within Formula II. Other suitable compounds include the following:

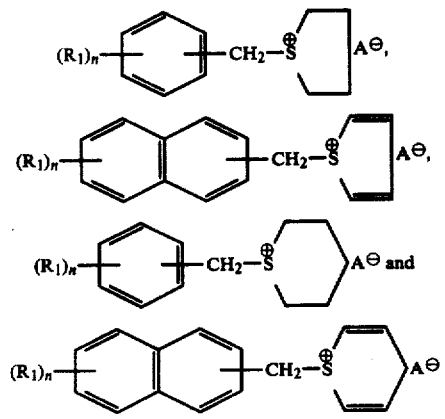

wherein n is 1 in each case and $R_1$ and $A^{\ominus}$ have the following values:

Table II

| $R_1$ | $A^{\ominus}$ |
|---|---|
| $C_6H_{13}$ | Cl |
| $C_8H_{17}$ | Br |
| $C_{10}H_{21}$ | I |
| $C_{12}H_{25}$ | $HSO_4$ |
| $C_{18}H_{37}$ | Cl |

The above examples are merely illustrative and other like compounds within I and II will be so readily apparent to those skilled in the art.

The acid solutions suitable for use herein are aqueous solutions of non-oxidizing inorganic acids, such as HF, HCl, $H_2SO_4$, $H_3PO_4$, etc., and mixtures thereof (oxidizing inorganic acids include $HNO_3$, $HClO_4$, $CrO_3$, etc.); or aqueous solutions of organic acids, such as formic acid acetic acid, sulfamic acid, hydroxy acetic, citric acid, etc., and mixtures thereof; or are aqueous solutions of known chelating agents, such as ethylenediaminetetraacetic acid, hereafter EDTA (and the ammonium, amine, or alkali metal salts of EDTA), and other like polyaminepolycarboxylic acids and the like; and mixtures of such aqueous acid solutions. The most common cleaning solutions are aqueous solutions of HCl and aqueous solutions of EDTA and amine or alkali metal salts of EDTA. The acid solutions may be buffered to maintain a desired pH level with conventional buffering agents, such as citric acid, acetic acid, and salts thereof. The pH values of acid cleaning solutions typically range from 1 to 5 for aqueous solutions of organic acids, and from pH 2–5 for aqueous solutions of chelating agents, such as the EDTA type cleaning solutions. The normality of cleaning solutions using inorganic acids are typically greater than 1.

The concentration of sulfonium salt used in the acid solutions may vary depending upon the particular salt, the particular metal and the degree of corrosion inhibition desired. Typically, concentrations of from about $1\times10^{-6}$ to about 0.1 moles of sulfonium salt per liter of solution are sufficient and concentrations of from about $1\times10^{-4}$ to 0.01 moles/liter are generally preferred.

The following examples further illustrate the invention.

GENERAL PROCEDURE

Coupons of carbon steel (having 98.7% Fe; 0.3% Mn; and 0.05% C.) having approximately 40 square centimeters of surface area were (a) scrubbed thoroughly with a soap-filled pad of steel wool in warm water, (b) rinsed with water, (c) washed with acetone, (d) pickled for 5 minutes in 10% aqueous HCl, (e) dried in air, and (f) weighed. The coupons thus prepared were then suspended from glass hooks in a stirred acid cleaning solution at 25° C. or 50° C. for normally 16 hours; the coupons being completely immersed in the solution. The coupons were then removed from the acid solutions, washed with soap and warm water, rinsed, dried and weighed. The weight loss resulting from such treatment is a measure of corrosion. The weight loss rate (WLR), having the units lbs./ft$^2$/day is determined as follows:

$$WLR = \frac{(49.15)\ (\text{weight loss in gm.})}{(\text{original weight in gm.})\ (SF)\ (\text{time})},$$

wherein (a) 49.15 is a conversion factor for converting gm./cm.$^2$/hr. to lbs./ft$^2$/day; (b) SF=strip factor=average ratio of surface area (cm.$^2$) to weight (gm.); and (c) the time is measured in hours. The quantity of acid cleaning solution in each case was approximately 1400 milliliters.

The effectiveness of the sulfonium salts was determined by comparing the WLR of a cleaning solution containing the sulfonium salts (WLR (test)) against the WLR of an identical cleaning solution without the sulfonium salts (WLR (blank)). The comparative data is reported as the "Percent Protection" which is calculated as follows:

$$\text{Percent Protection} = \frac{WLR\ (\text{blank}) - WLR\ (\text{test})}{WLR\ (\text{blank})} \times 100.$$

The sulfonium salts were evaluated in three representative acid cleaning solutions. Solution "A" was a 3.8 percent by weight, total weight basis, aqueous solution of an ammonium salt of ethylenediaminetetracetic acid buffered at a pH of 5 with citric acid and contained 0.10 percent by weight, total weight basis, of $Fe^{+3}$ (added as $FeNH_4(SO_4)_2$. 12 $H_2O$). Solution "B" was a 10 percent by weight, total weight basis, aqueous solution of HCl, and 0.10 percent by weight of $Fe^{+3}$ (added as $FeCl_3$). Solution "C" was a 10 percent by weight, total weight basis, aqueous solution of $H_2SO_4$ and 0.1 percent by weight of $Fe^{+3}$ (added as $FeNH_4(SO_4)_2$. $12H_2O$).

EXPERIMENTS 1–10

The results of several experiments conducted in accordance with the above general procedure and using solution "A" containing various inhibitors are tabulated in Table III. The sulfonium salts used in this series of experiments correspond to Formula I wherein n is 1, $A^{\ominus}$ is chloride and $R_1$–$R_3$are as designated in the table. The concentration of the sulfonium salts in the test solutions is listed in Table III (and the remaining tables herein) under the heading "Conc." and is expressed in millimoles (m-moles) per liter. The steel metal coupons having the above assay were used in every one of the following examples unless otherwise specified.

Table III

| Ex. | $R_1$ | $R_2$ | $R_3$ | Conc. | Temp. (°C.) | WLR (Test) | % Protection |
|---|---|---|---|---|---|---|---|
| 1 | $CH_3$ | $C_{12}H_{25}$ | $CH_3$ | 0.40 | 25 | 0.0571 | 26 |
| 2 | i-$C_3H_7$ | $C_{12}H_{25}$ | $CH_3$ | 0.40 | 25 | 0.0267 | 64 |
| 3 | p-n-$C_8H_{17}$ | $CH_3$ | $CH_3$ | 0.69 | 50 | 0.0054 | 89 |
| 4 | p-n-$C_{12}H_{25}$ | $CH_3$ | 0.20 | 25 | 0.0020 | 95 | |
| 5 | p-n-$C_{12}H_{25}$ | $CH_3$ | $CH_3$ | 0.30 | 50 | 0.0090 | 82 |
| 6 | p-n-$C_{12}H_{25}$ | $CH_3$ | n-$C_4H_9$ | 0.40 | 25 | 0.0039 | 90 |
| 7 | p-n-$C_{12}H_{25}$ | $CH_2CH_2OH$ | $CH_2CH_2OH$ | 0.20 | 25 | 0.003 | 93 |
| 8 | p-n-$C_{12}H_{25}$ | n-$C_4H_4$ | n-$C_4H_9$ | 0.40 | 25 | 0.025 | 34 |
| 9 | p-n-$C_{12}H_{25}$ | n-$C_{12}H_{25}$ | $CH_3$ | 0.04 | 25 | 0.072 | 6 |
| 10 | p-$C_{17}H_{35}$ | $CH_3$ | $CH_3$ | 0.30 | 50 | 0.020 | 61 |

In experiments 4–9, the $R_1$ radical was actually a mixture of $C_8$–$C_{18}$ alkyl radicals with $C_{12}H_{25}$ being the predominant species.

EXPERIMENTS 11

In like manner, benzyldodecylmethylsulfonium bromide gave 8 percent protection under similar circumstances (solution "A", Conc.=0.4, 25° C., WLR of 0.035).

EXPERIMENTS 12–15

In like manner, certain sulfonium salts represented by I were shown to be effective in inhibiting corrosion by solution "B". In each instance, $A^{\ominus}$ is chloride and n is 1 in Formula I. Data are in Table IV below:

Table TV

| Ex. | $R_1$ | $R_2$ | $R_3$ | Conc. | Temp. (°C.) | WLR (Test) | % Protection |
|---|---|---|---|---|---|---|---|
| 12 | p-n-$C_{12}H_{25}$ | $CH_3$ | $CH_3$ | 0.20 | 25 | 0.020 | 52 |
| 13 | p-n-$C_{12}H_{25}$ | $CH_{CH3}$ | 0.39 | 0.39 | 50 | 0.021 | 69 |
| 14 | p-n-$C_2H_{17}$ | $CH_3$ | $CH_3$ | 0.40 | 25 | 0.029 | 52 |
| 15 | p-n-$C_{12}H_{25}$ | $CH_2CH_2OH$ | $CH_2CH_2OH$ | 0.40 | 25 | 0.018 | 56 |

EXPERIMENTS 16–17

In like manner, certain sulfonium salts represented by I were shown to be effective in inhibiting corrosion by solution "C". In each instance, $A^{\ominus}$ is chloride and n is 1 in Formula I. Data are in Table V below:

Table V

| Ex. | $R_1$ | $R_2$ | $R_3$ | Conc. | Temp. (°C.) | WLR (Test) | % Protection |
|---|---|---|---|---|---|---|---|
| 16 | p-n-$C_{12}H_{25}$ | $CH_3$ | $CH_3$ | 0.40 | 25 | 0.003 | 94 |
| 17 | p-n-$C_3H_{17}$ | $CH_3$ | $CH_3$ | 0.40 | 25 | 0.009 | 93 |

EXPERIMENTS 18–23

In other experiments, test solution "A" containing p-n-dodecylbenzyldimethylsulfonium chloride as the inhibitor was evaluated in a "flow test" wherein the solution was pumped through steel pipes for 6 to 7 hours and the degree of corrosion determined as above. The steel pipes used in this test were sections cut from the same length of pipe and measured approximately 1 foot in length and 0.75 inch in inside diameter. The pipes were cleaned free of rust by use of a commercial cleaning solution quite similar to solution "A" except that no $Fe^{+3}$ was added, and were scrubbed with soap and warm water, rinsed with water, rinsed with acetone, dried and weighed. After the flow test, the pipes were again scrubbed, rinsed with water, rinsed with acetone, dried and weighed. The "WLR" and "Percent Protection" were calculated as above. The results are summarized in Table VI below. The flow rate is measured in gallons/minute and the concentration of sulfonium salt (Conc.) is expressed as millimoles per liter.

Table VI

| Ex. | Flow Rate | Temp. (°C.) | Inhibitor Conc. | WLR (Test) | Percent Protection |
|---|---|---|---|---|---|
| 18 | 0.2 | 25 | 0.39 | 0.011 | 89 |
| 19 | 0.2 | 50 | 0.39 | 0.016 | 81 |
| 20 | 0.2 | 65 | 0.56 | 0.014 | 86 |
| 21 | 5.0 | 25 | 0.39 | 0.0064 | 97 |
| 22 | 5.0 | 65 | 0.56 | 0.028 | 95 |
| 23 | 10.0 | 25 | 0.39 | 0.0064 | 99 |

EXPERIMENTS 24–26

In still other experiments, the subject sulfonium salts were evaluated as corrosion inhibitors in aqueous acid solutions which did not initially contain any significant amount of ferric ion. Experiments 24 and 25 were conducted in 10 percent by weight, total weight basis, aqueous HCl solutions and experiment 26 was conducted in a 10 percent by weight aqueous $H_2SO_4$ solution. In each of experiments 24–26, the inhibitor was p-dodecylbenzyldimethylsulfonium chloride and the metal coupons and the testing procedure used were substantially the same as described in experiments 1–10. The results are tabulated in Table VII below. The concentration (Conc.) of sulfonium salt is expressed in millimoles per liter.

Table VII

| Ex. | Inhibitor Conc. | Temp. °C. | WLR (Test) | Percent Protection |
|---|---|---|---|---|
| 24 | 0.28 | 25 | 0.0027 | 91 |
| 25 | 0.36 | 50 | 0.0047 | 98 |
| 26 | 0.30 | 25 | 0.0031 | 75 |

EXPERIMENT 27

Using substantially the same procedure and test conditions as in experiment 2, the corrosion of a copper alloy (78% Cu, 21% Zn, and 1% Sn) in contact with solution "A" at 25° C. was found to be inhibited by p-dodecylbenzyldimethylsulfonium chloride (Conc.=0.4 mmoles/liter). WLR (Test)=0.0003. Percent Protection=96%.

EXPERIMENT 28

Using substantially the same procedure and test conditions as in experiment 2, the corrosion of a ferrous metal coupon (having the aforesaid analysis) in contact with an aqueous 5 percent phosphoric acid solution at 25° C. was found to be inhibited by p-dodecylbenzyldimethylsulfonium chloride (Conc.=0.4 mmoles/liter). WLR (Test)=0.003. Percent Protection=63%.

EXPERIMENTS 29–31

Using substantially the same procedures and test conditions as detailed in experiments 2, 10 and 15, the corrosion of ferrous metal coupons (having the aforesaid analysis) in contact with solution A, B or C was inhibited by using p-n-dodecylbenzylthiophenium chloride

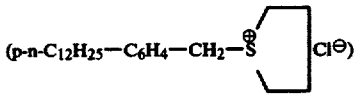

at a concentration of 0.40 mmoles per liter. The temperature in each instance was 25° C. Data are reported in Table VIII.

Table VIII

| Ex. | Acidic Solution | Percent Protection |
|---|---|---|
| 29 | A | 94 |
| 30 | B | 49 |
| 31 | C | 95 |

EXPERIMENTS 32–33

Two other sulfonium salts were evaluated using substantially the same procedure and test conditions detailed in experiment 12 (except that the acid solution was 5% HCl containing 0.3% $Fe^{+3}$ as ferric chloride instead of 0.1% of $Fe^{+3}$). p-n-Dodecylbenzyldiallylsulfonium chloride gave 42 percent protection and

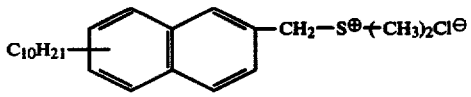

gave 71 percent protection. The temperature was 25° C. and the concentration of sulfonium salt in the acid medium was about 0.2 mmoles per liter in each instance.

EXPERIMENTS 34–35

Using substantially the same procedure and test conditions as detailed in experiment 2, the sulfonium salt

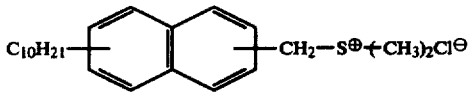

was evaluated as an inhibitor at a concentration of 0.4 mmoles/liter in solutions "B" and "C" at a temperature of 25° C. The sulfonium salt gave 81 percent and 92 percent protection in solutions "B" and "C", respectively.

EXPERIMENTS 36–37

Using substantially the same procedure and test conditions detailed in experiment 2, p-dodecylbenzyldodecylmethylsulfonium chloride was evaluated as an inhibitor at a concentration of 0.4 mmoles/liter in solutions "B" and "C" at 25° C. It gave 29 percent and 57 percent protection in solutions "B" and "C", respectively.

In the above examples, a thin, adherent, hydrophobic protective film was generally observed on the ferrous articles cleaned with the inhibited cleaning solutions. The film was predominantly a mixture of compounds of the formula

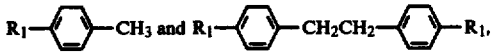

wherein $R_1$ had the designated meaning in the examples. E.g., coupons cleaned with the test solutions inhibited with p-dodecylbenzyldimethylsulfonium chloride were observed to have a protective film of (predominantly) (p,p'-bisdodecyl)bibenzyl and p-dodecyltoluene on their surface; such coupons were suspended over water in a closed vessel for 11 days and showed only small localized rust spots while coupons cleaned with the uninhibited solutions and concurrently aged over water were uniformly covered with red rust.

EXPERIMENTS 38–39

Using substantially the same procedure and test conditions detailed in experiment 2, the sulfonium salt

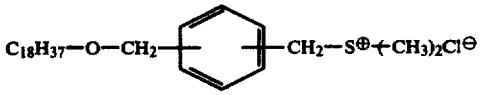

was evaluated as an inhibitor at a concentration of 0.4 mmoles/liter in solutions "A" and "B". The sulfonium salt gave 73 percent (WLR Test=0.021) and 43 percent (WLR Test=0.025) protection in solutions "A" and "B", respectively. Temperature, 25° C.

EXPERIMENTS 40–42

Using substantially the same procedure and test conditions detailed in experiment 2, phenoxybenzyldimethylsulfonium chloride was evaluated as an inhibitor at a concentration of 0.4 mmoles in 10 percent aqueous HCl at 25° C. It gave 87 percent protection (WLR Test=0.010). Using the same salt in solutions "A" and "B", the percent protection was 70 percent and 60 percent, respectively.

EXPERIMENTS 43–45

Using substantially the same procedure and test conditions detailed in experiment 2, dodecylphenoxybenzyldimethylsulfonium chloride was evaluated as an inhibitor at a concentration of 0.4 mmoles/liter in solutions "A" and "B" at 25° C. It gave 87 percent and 43 percent protection in solutions "A" and "B", respectively.

EXPERIMENTS 46–47

Using substantially the same procedure and test conditions detailed in experiment 2, the effectiveness of sulfonium salts corresponding to the formula

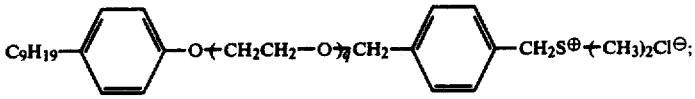

wherein q=4 or 7, was evaluated. The data are reported in Table IX.

Table IX

| Ex. | g | Conc. | Temp. (°C.) | WLR (Test) | Percent Protection |
|---|---|---|---|---|---|
| 46 | 4 | 0.40 | 25 | 0.013 | 83 |
| 47 | 7 | 0.40 | 25 | 0.026 | 65 |

The test solution in these experiments was solution "A".

The compounds used in experiments 46 and 47 are illustrative of sulfonium salts corresponding to the general formula

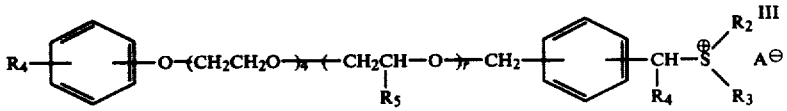

III wherein: $R_2$ and $R_3$ have the aforesaid meaning; $R_4$ is alkyl of 4 to about 20 carbon atoms; $R_5$ is methyl or ethyl; $R_6$ is hydrogen, methyl or ethyl; q is an integer of from 0 to 8; r is an integer of from 0 to 10; with the proviso that the sum of q plus r is equal to or less than 10. Such compounds are conveniently prepared by reacting a xylyl dihalide (e.g. $ClCH_2—C_6H_4—CH_2Cl$) with the sodium alcoholate of an alkoxylated alkylphenol under conventional conditions for a Williamson ether synthesis. The product thus formed is then reacted with $R_2—S—R_3$ to form III, the desired sulfonium compounds.

The above data show that sulfonium salts corresponding to Formulas I–III are effective in inhibiting the corrosion of ferrous and cuprous metals in contact with acidic cleaning solutions and ferric ions. Such experiments are not all inclusive but are merely meant to be illustrative. Other sulfoniums within Formulas I–III can be similarly used.

We claim:

1. An aqueous acidic cleaning solution of at least one organic acid having dissolved or dispersed therein a sulfonium salt corresponding to the formula

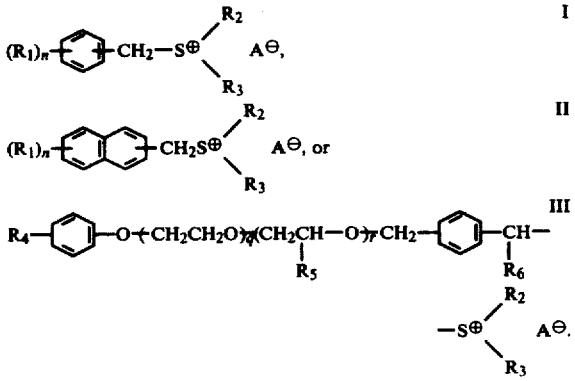

I

II

III wherein n is 1 or 2; each $R_1$ independently is hydrogen or a hydrocarbyl, a hydrocarbyl whose chain length is interrupted by an atom of oxygen or sulfur, a hydrocarbyloxyor a hydrocarbylthio radical of from 1 to about 24 carbon atoms; $R_2$ is a hydrocarbyl or inertly-substituted hydrocarbyl radical of from 1 to about 24 carbon atoms, with the proviso that the total aggregate carbon content of $R_1$ and $R_2$ is from 7 to about 25; $R_3$ is an alkyl radical of from 1 to 4 carbon atoms or an inertly-substituted alkyl radical of from 2 to 4 carbon atoms, allyl, phenyl or an inertly-substituted phenyl radical; or $R_2$ and $R_3$ are joined to form a 5- or 6-membered heterocyclic ring, with the proviso that the total aggregate carbon content of $R_1$, $R_2$ and $R_3$ is from 10 to about 25; $R_4$ is alkyl of 4 to about 20 carbon atoms; $R_5$ is methyl or ethyl; $R_6$ is hydrogen, methyl or ethyl; q is an integer of from 0 to 8; r is an integer of from 0 to 10, with the proviso that the sum of q plus r is equal to or less than 10; and $A^{\ominus}$ is an anion; said sulfonium salt being present in an amount at least sufficient to inhibit the acid-induced corrosion of ferrous metals in contact with said solution and ferric ions.

2. The composition defined by claim 1 wherein said sulfonium salt corresponds to Formula I.

3. The composition defined by claim 1 wherein said sulfonium salt corresponds to Formula II.

4. The composition defined by claim 1 wherein said sulfonium salt corresponds to Formula III.

5. The composition defined by claim 1 wherein said sulfonium salt corresponds to Formula I or II and wherein n is 1; $R_1$ is hydrogen, alkyl or alkylphenoxy; $R_2$ is alkyl, β-hydroxyethyl or allyl; $R_3$ is alkyl, β-hydroxyethyl or allyl.

6. In the process of treating ferrous metal surfaces to remove iron oxide encrustations by treating said metal surface with an aqueous acid cleaning solution, the improvement consisting of using the composition defined by claim 1 as said cleaning solution.

7. The composition defined by claim 1 wherein n is 1 and said sulfonium salt corresponds to Formula I and II.

8. The composition defined by claim 7 wherein $R_1$ is hydrogen, alkyl or alkylphenoxy.

9. The composition defined by claim 8 wherein $R_1$ is alkyl of from 8 to 18 carbon atoms.

10. The composition defined by claim 1 wherein $R_2$ is alkyl, β-hydroxyalkyl of 2 to 4 carbon atoms, allyl, phenyl or hydroxyphenyl.

11. The composition defined by claim 10 wherein $R_2$ is alkyl, β-hydroxyethyl or allyl.

12. The composition defined by claim 10 in which $R_2$ and $R_3$ are each alkyl.

13. The composition defined by claim 1 wherein $R_3$ is alkyl, β-hydroxyalkyl of 2 to 4 carbon atoms, allyl, phenyl or hydroxyphenyl.

14. The composition defined by claim 13 wherein $R_3$ is alkyl, β-hydroxyethyl or allyl.

15. The composition defined by claim 14 wherein said sulfonium salt corresponds to Formula I; $R_1$ is alkyl of 8 to 18 carbon atoms; and $R_2$ and $R_3$ are alkyl of 1 to 4 carbon atoms, β-hydroxyethyl or allyl.

16. The composition defined by claim 1 wherein said acid is an aqueous solution of an organic carboxylic or polycarboxylic acid or a mixture thereof.

17. The composition defined by claim 16 wherein said acid is an aqueous solution of a polyaminepolycarboxylic acid or an ammonium-, amine-, or alkali metal salt thereof, or mixtures thereof.

18. The composition defined by claim 17 wherein said acid is an aqueous solution of ethylenediaminetetraacetic acid (EDTA) or the ammonium-, amine-, or alkali metal salt thereof.

19. A process of inhibiting the acid-induced and ferric ion-induced corrosion of metal surfaces in contact with an aqueous acid solution of at least one organic acid, the process comprising incorporating in said acid solution a small but corrosion-inhibiting amount of at least one sulfonium salt corresponding to the formula

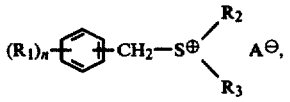

I

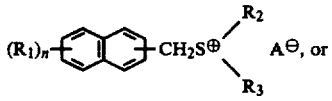

II

-continued

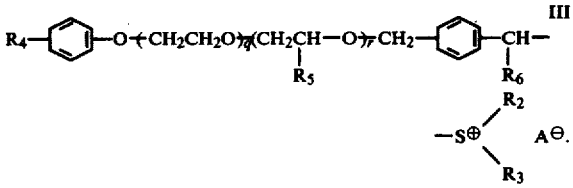

III wherein n is 1 or 2; each $R_1$ independently is hydrogen or a hydrocarbyl, a hydrocarbyl whose chain length is interrupted by an atom of oxygen or sulfur, a hydrocarbyloxy or a hydrocarbylthio radical of from 1 to about 24 carbon atoms; $R_2$ is a hydrocarbyl or inertly-substituted hydrocarbyl radical of from 1 to about 24 carbon atoms, with the proviso that the total aggregate carbon content of $R_1$ and $R_2$ is from 7 to about 25; $R_3$ is an alkyl radical of from 1 to 4 carbon atoms or an inertly-substituted alkyl radical of from 2 to 4 carbon atoms, allyl, phenyl or an inertly-substituted phenyl radical; or $R_2$ and $R_3$ are joined to form a 5- or 6-membered heterocyclic ring, with the proviso that the total aggregate carbon content of $R_1$, $R_2$ and $R_3$ is from 10 to about 25; $R_4$ is alkyl of 4 to about 20 carbon atoms; $R_5$ is methyl or ethyl; $R_6$ is hydrogen, methyl or ethyl; q is an integer of from 1 to 8; r is an integer of from 0 to 12, with the proviso that the sum of q plus r is equal to or less than 12; and $A^{\ominus}$ is an anion; said sulfonium salt being present in an amount at least sufficient to inhibit the acid-induced corrosion of ferrous metals in contact with said solution and ferric ions.

20. The process defined by claim 19 in which $R_2$ and $R_3$ are each alkyl.

* * * * *

UNITED STATES PATENT AND TRADEMARK OFFICE

CERTIFICATE OF CORRECTION

PATENT NO. : REISSUE 30,283

DATED : May 27, 1980

INVENTOR(S) : Wayne W. Frenier and William J. Settineri

It is certified that error appears in the above-identified patent and that said Letters Patent are hereby corrected as shown below:

Col. 1, line 57, "clearing" should read -- cleaning --;

Col. 3, line 22, insert "," after "phenethyl";

Col. 4, Table I, fourth compound in column 1, "$C_3H_{17}$" should read -- $C_8H_{17}$ --;

Col. 4, Table I, fifteenth compound in column 4, "$NO_1$" should read -- $NO_3$ --;

Col. 6, line 62, "$R_1$-$R_3$are" should read -- $R_1$-$R_3$ are --;

Col. 7, Table III, Ex. 4, the last five columns in the Table should read as follows:

| $R_3$ | Conc. | Temp. (°C.) | WLR (Test) | % Protection |
|---|---|---|---|---|
| $CH_3$ | 0.20 | 25 | 0.0020 | 95 |

Col. 7, Table III, Ex. 8 under column heading "$R_2$", "n-$C_4H_4$" should read -- n-$C_4$-$H_9$ --;

Col. 7, Table III, Ex. 9 under column heading "Conc.", "0.04" should read -- 0.40 --;

Col. 7, line 18, title "EXPERIMENTS 11" should read -- EXPERIMENT 11 --;

Col. 7, line 30, "Table TV" should read -- Table IV --;

UNITED STATES PATENT AND TRADEMARK OFFICE

CERTIFICATE OF CORRECTION

PATENT NO. : REISSUE 30,283

DATED : May 27, 1980

INVENTOR(S) : Wayne W. Frenier and William J. Settineri

It is certified that error appears in the above-identified patent and that said Letters Patent are hereby corrected as shown below:

Col. 7, Table IV, Ex. 13 under columns "$R_2$" and "$R_3$", "$CH_{CH3}$" and "0.39" should read -- $CH_3$ -- and --$CH_3$-- respectively;

Col. 7, Table IV, Ex. 14 under column "$R_1$", "p-n-$C_2H_{17}$" should read -- p-n-$C_8H_{17}$ --;

Col. 7, Table V, Ex. 16 under column "WLR (Test)", "0.003" should read -- 0.008 --;

Col. 7, Table V, Ex. 17 under column "$R_1$", "p-n-$C_3H_{17}$" should read -- p-n-$C_8H_{17}$ --;

Col. 11, lines 20-25, Formula III should read as follows:

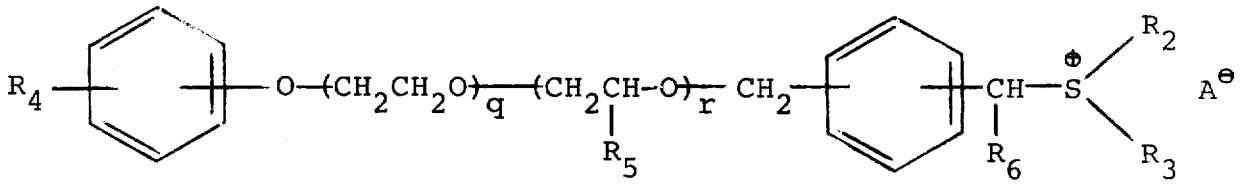

Col. 12, line 7, "byloxyor" should read -- byloxy or --;

UNITED STATES PATENT AND TRADEMARK OFFICE

CERTIFICATE OF CORRECTION

PATENT NO. : REISSUE 30,283

DATED : May 27, 1980

INVENTOR(S) : Wayne W. Frenier and William J. Settineri

It is certified that error appears in the above-identified patent and that said Letters Patent are hereby corrected as shown below:

Col. 12, line 52, "Formula I and II" should read -- Formula I or II --.

Signed and Sealed this

*Twenty-third* Day of *September 1980*

[SEAL]

*Attest:*

SIDNEY A. DIAMOND

*Attesting Officer*

*Commissioner of Patents and Trademarks*